US009694190B2

(12) United States Patent
Tolosa et al.

(10) Patent No.: US 9,694,190 B2
(45) Date of Patent: Jul. 4, 2017

(54) METHOD TO PATTERN <10 MICROMETER CONDUCTING AND PASSIVATING FEATURES ON 3D SUBSTRATES FOR IMPLANTABLE DEVICES

(71) Applicant: Lawrence Livermore National Security, LLC, Livermore, CA (US)

(72) Inventors: Vanessa Tolosa, Oakland, CA (US); Satinderpall S. Pannu, Pleasanton, CA (US); Heeral Sheth, Oakland, CA (US); Angela C. Tooker, Dublin, CA (US); Kedar G. Shah, San Francisco, CA (US); Sarah H. Felix, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 14/213,733

(22) Filed: Mar. 14, 2014

(65) Prior Publication Data

US 2016/0082271 A1 Mar. 24, 2016

Related U.S. Application Data

(60) Provisional application No. 61/802,037, filed on Mar. 15, 2013.

(51) Int. Cl.
*A61N 1/05* (2006.01)
*A61N 1/375* (2006.01)
*H05K 3/02* (2006.01)
*H05K 3/28* (2006.01)

(52) U.S. Cl.
CPC .............. *A61N 1/3756* (2013.01); *A61N 1/05* (2013.01); *H05K 3/02* (2013.01); *H05K 3/28* (2013.01)

(58) Field of Classification Search
CPC ........................................................ A61N 1/05
USPC ............. 427/425, 58; 607/116; 118/320, 321
See application file for complete search history.

(56) References Cited

U.S. PATENT DOCUMENTS

| 5,522,847 | A | 6/1996 | Gates |
| 5,660,163 | A | 8/1997 | Sculman et al. |
| 5,693,577 | A | 12/1997 | Krenik et al. |
| 6,024,702 | A * | 2/2000 | Iversen ................ A61B 5/0422 600/378 |
| 6,071,347 | A * | 6/2000 | Ogawa .................. B29C 41/085 118/304 |
| 6,259,937 | B1 * | 7/2001 | Schulman .......... A61B 5/14532 600/300 |
| 7,085,605 | B2 * | 8/2006 | Bluger ................. A61N 1/0541 607/116 |

(Continued)

FOREIGN PATENT DOCUMENTS

JP 2003-526491 9/2003

OTHER PUBLICATIONS

International Search Report and Written Opinion for PCT/US14/030665, corresponding to U.S. Appl. 14/213,733, 10 pages.

*Primary Examiner* — Cachet Sellman
(74) *Attorney, Agent, or Firm* — Eddie E. Scott

(57) ABSTRACT

An implantable device has a cylindrical base, at least one electrode on the cylindrical base, at least one electrically conducting lead on the cylindrical base connected to the electrode wherein the electrically conducting lead has a feature size of <10 micrometers. A protective coating on the cylindrical base covers the at least one electrically conducting lead.

16 Claims, 5 Drawing Sheets

(56) References Cited

U.S. PATENT DOCUMENTS

| | | | |
|---|---|---|---|
| 8,099,172 B2* | 1/2012 | Swanson | A61N 1/0553 607/116 |
| 8,209,023 B2* | 6/2012 | Zhou | 607/115 |
| 8,371,241 B2* | 2/2013 | Sedberry | H01Q 1/42 118/320 |
| 2003/0018381 A1* | 1/2003 | Whitcher | C23C 14/562 623/1.15 |
| 2006/0206165 A1* | 9/2006 | Jaax | A61N 1/0529 607/46 |
| 2009/0227885 A1* | 9/2009 | Lowery | A61B 5/029 600/526 |
| 2010/0114278 A1* | 5/2010 | McMorrow | A61N 1/0553 607/116 |
| 2011/0072659 A1* | 3/2011 | Swanson | A61N 1/05 29/885 |
| 2011/0230747 A1* | 9/2011 | Rogers | A61B 5/05 600/377 |
| 2012/0055257 A1* | 3/2012 | Shaw-Klein | H01L 41/081 73/780 |
| 2014/0172057 A1* | 6/2014 | Orinski | A61N 1/0553 607/116 |

\* cited by examiner

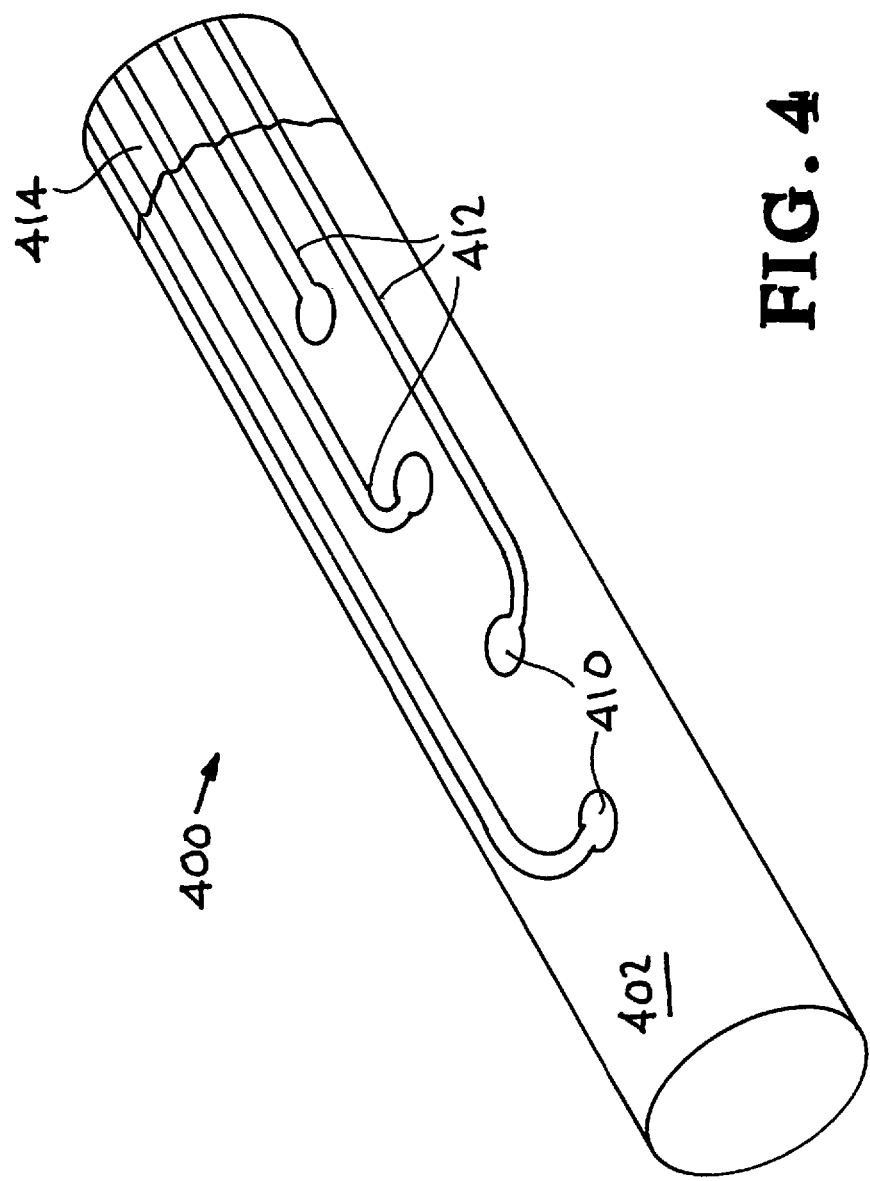

METHOD TO PATTERN <10 MICROMETER CONDUCTING AND PASSIVATING FEATURES ON 3D SUBSTRATES FOR IMPLANTABLE DEVICES

CROSS-REFERENCE TO RELATED APPLICATIONS

This application claims benefit under 35 U.S.C. §119(e) of U.S. Provisional Patent Application No. 61/802,037 filed Mar. 15, 2013 entitled "method to pattern <10 micrometer conducting and passivating features on 3D substrates for implantable devices," the disclosure of which is hereby incorporated by reference in its entirety for all purposes.

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present application relates to implantable devices and methods of fabricating implantable devices, and particularly to methods for patterning <10 micrometer conducting and passivating features on 3D substrates for implantable devices.

State of Technology

This section provides background information related to the present disclosure which is not necessarily prior art.

The current methods to pattern micron-sized features have involved lithographic techniques and printing technologies. These techniques are suitable for patterning materials on flat surfaces with relatively large feature sizes, however, the limitations of both methods prevent the ease and reliable patterning of smaller feature sizes on non-planar substrates. Lithographic techniques require several steps often involving harmful chemicals. Screen and ink-jet printing require planar substrates and are limited to tens of microns in resolution. Lithography and screen printing require masks that have to be custom-made for each new design.

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

There is a need for the ability to prepare patterns of materials with feature sizes <10 microns on 3D substrates. The materials must include metals, dielectrics, and polymers and the method must be highly repeatable, accurate, and relatively simple.

Applicant's apparatus, system and methods provide an implantable device having a cylindrical base, at least one electrode on the cylindrical base, at least one electrically conducting lead on the cylindrical base connected to the electrode wherein the electrically conducting lead has a feature size of <10 micrometers, and a protective coating on the cylindrical base covering the at least one electrically conducting lead. In one embodiment Applicant's implantable device is fabricated by providing a base, providing a rotation system for rotating the base, providing a deposition system for depositing material on the base, using the rotation system and the deposition system to deposit at least one electrode on the base, using the rotation system and the deposition system to deposit at least one electrically conducting lead on the base coupled to the at least one electrode, and using the rotation system and the deposition system to deposit a protective coating on the base covering the at least one electrically conducting lead. In another embodiment Applicant's implantable device is fabricated by providing a base, providing a rotation system for rotating the base, providing a coating system for coating the base, providing an ablating system for ablating at least a portion of the coating, using the rotation system, the coating system, and the ablating system to form at least one electrode on the base, using the rotation system, the coating system, and the ablating system to form at least one electrically conducting lead on the base coupled to the at least one electrode, and using the rotation system and the coating system deposit a protective coating on the base covering the at least one electrically conducting lead.

Applicant's apparatus, system and methods have use in the fabrication of implantable biomedical devices, specifically for interfacing with neurons and other excitable cells. Applicant's apparatus, system and methods can be applied to the manufacturing of any device requiring <10 micron-sized features on 3D substrates using a relatively simple method.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

FIG. 4 illustrates an embodiment of Applicant's implantable device with <10 micrometer conducting and passivating features on a 3D substrate.

DETAILED DESCRIPTION OF SPECIFIC EMBODIMENTS

Figure 1A:
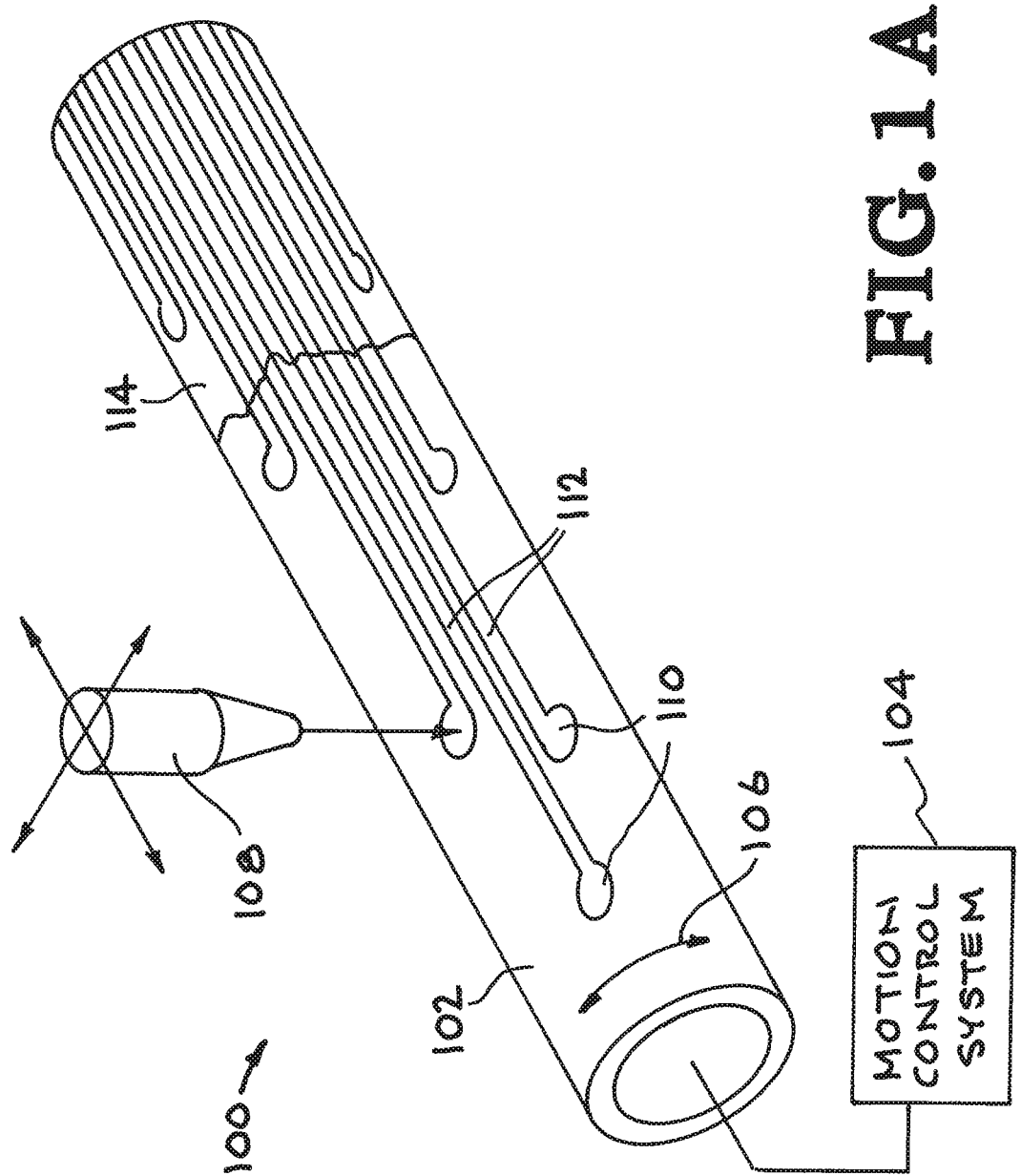
FIG. 1A and FIG. 1B illustrate one embodiment of Applicant's method to pattern <10 micrometer conducting and passivating features on 3D substrates for implantable devices.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

Applicant's apparatus, system and methods address the need to pattern a variety of materials with small feature sizes on non-planar substrates. The materials include metals, dielectrics, and polymers and the method should be highly repeatable, accurate, and relatively simple. Applicant's apparatus, system and methods involve two methods to create patterned materials on 3D substrates. The first method utilizes an additive deposition method called direct ink writing. It involves the use of a precise motion control system to deposit specially developed ink through a syringe-like container. The materials (inks) are deposited in customized patterns on 3D substrates. The second method utilizes a subtractive method that involves patterning of materials deposited on a 3D structure by etching away the material by ablation or burning off.

Figure 1B:
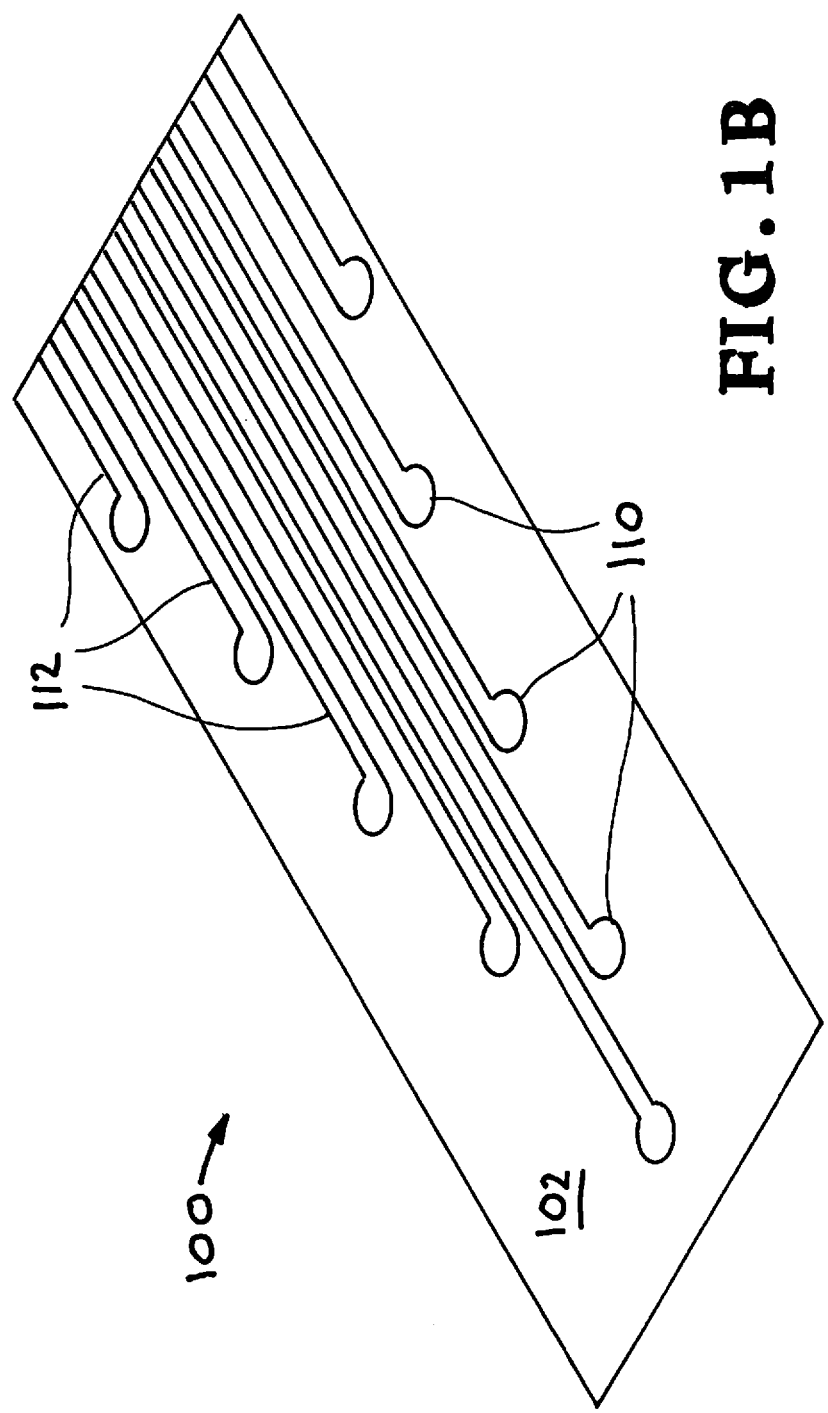

Referring now to the drawings and in particular to FIGS. 1A and 1B, one embodiment of Applicant's method for patterning <10 micrometer conducting and passivating features on a 3D substrate to produce an implantable device is illustrated. Applicant's implantable device is designated generally by the reference numeral 100.

Referring now to FIG. 1A, the method of fabricating Applicant's implantable device begins with a base 102. The base 102 is generally cylindrical. A motion control system 104 is provided for rotating the base 102. Rotation of the base is illustrated by the double headed arrow 106.

A precise deposition system 108 is used to deposit coatings and specially developed ink through a syringe-like container onto the base 102. Sensors 110 and conducting traces 112 are deposited on the base 102 using the motion control system 104 and the deposition system 108. As illustrated in FIG. 1A, the deposition system 108 deposits specially developed ink through a syringe-like container onto the base 102 to form the sensors 110 and the conducting traces 112.

After the sensors 110 and conducting traces 112 are deposited on the base 102 they are covered by depositing a protective coating 114 using the deposition system 108. Openings in the protective coating 114 for the sensors 110 are provided by controlling the deposition system 108 so that there is no protective coating 114 over the sensors 110.

Referring now to FIG. 1B, the method of fabricating Applicant's implantable device 100 is further illustrated by a flat, two dimensional view, of base 102, sensors 110, and conducting traces 112. If one was to unwrap the surface of the device 100 shown in FIG. 1A, you would see the pattern of sensors and traces that encircle the base 102. The sensors 110 and conducting traces 112 are shown on the base 102. Applicant's implantable device 100 can be used for implantable biomedical devices, specifically for interfacing with neurons and other excitable cells.

Figure 2:
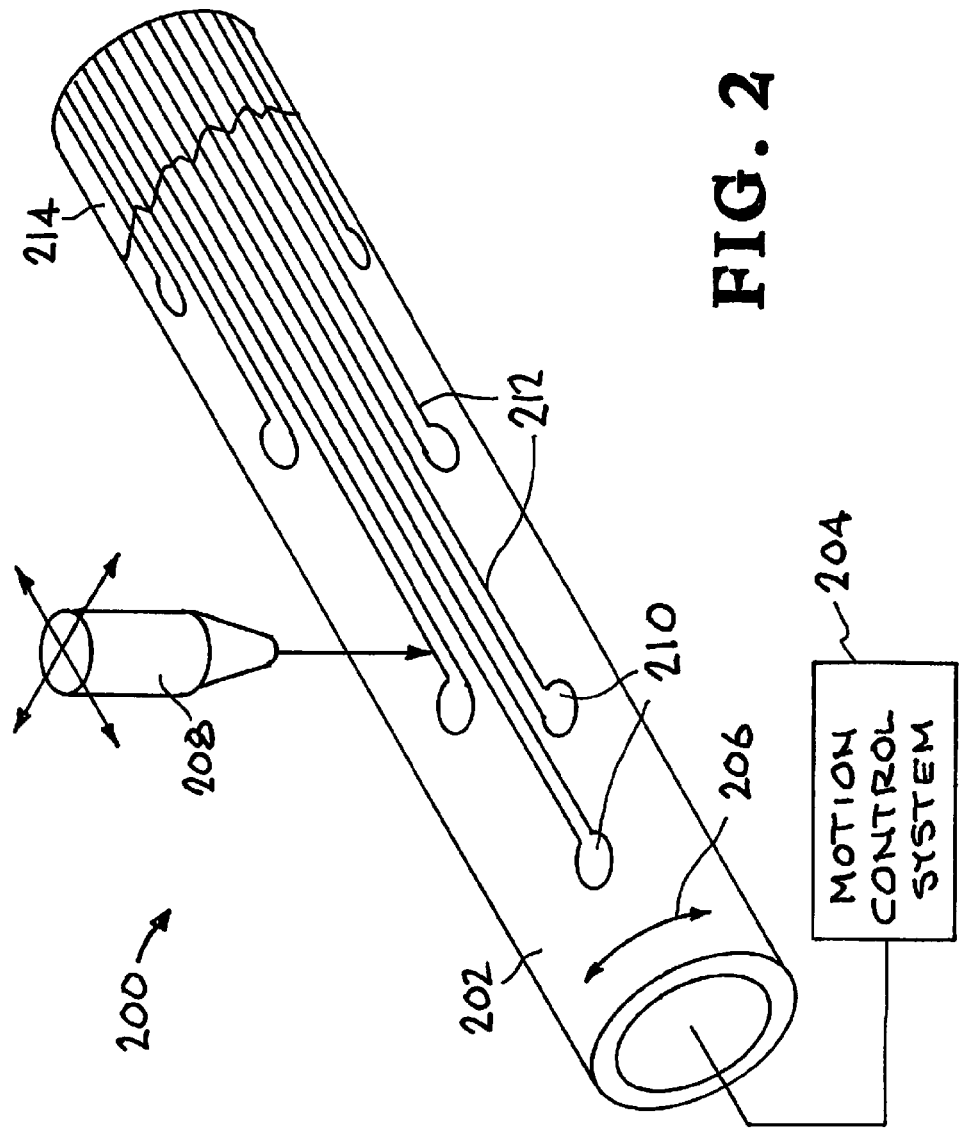
FIG. 2 illustrates another embodiment of Applicant's method to pattern <10 micrometer conducting and passivating features on 3D substrates for implantable devices.

Referring now to FIG. 2, another embodiment of Applicant's method of patterning <10 micrometer conducting and passivating features on 3D substrates for implantable devices is illustrated. This embodiment of Applicant's implantable device is designated generally by the reference numeral 200.

This embodiment of Applicant's method utilizes a subtractive method that involves patterning of materials deposited on a 3D structure by etching away the material by ablation or burning off. The material will be deposited on 3D substrates either by traditional deposition methods such as chemical vapor deposition, sputtering, spin coating, or e-beam/thermal evaporation deposition or by the direct ink write method described above. Patterning or further patterning will be performed by precise laser removal via ablation or heating. Vias and edges will be defined either by laser cutting completely through the material or layers of material or by removing only specific layers. Control of the laser patterning will require development of precise laser machining using technology like femtosecond laser pulsing.

The method of fabricating Applicant's implantable device 200 begins with a base 202. The base 202 is generally cylindrical. A system 204 is provided for rotating the base 202 as illustrated by the double headed arrow 206. An ablative system 208 such as a laser is used to etch away the material by ablation or heating. Sensors 210 and conducting traces 212 are formed on the base 202. Applicant's implantable device 200 is fabricated by the steps of providing a base, providing a rotation system for rotating the base, providing a coating system for coating the base, providing an ablating system for abating at least a portion of the coating, using the rotation system, the coating system, and the ablating to form at least one electrode on the base, and using the rotation system, the coating system, and the ablating to form at least one electrically conducting lead on the base coupled to the at least one electrode. After the sensors 210 and conducting traces 212 are formed on the base 202 they are covered by depositing a protective coating 214. Openings in the protective coating 214 for the sensors 210 are provided.

Figure 3:
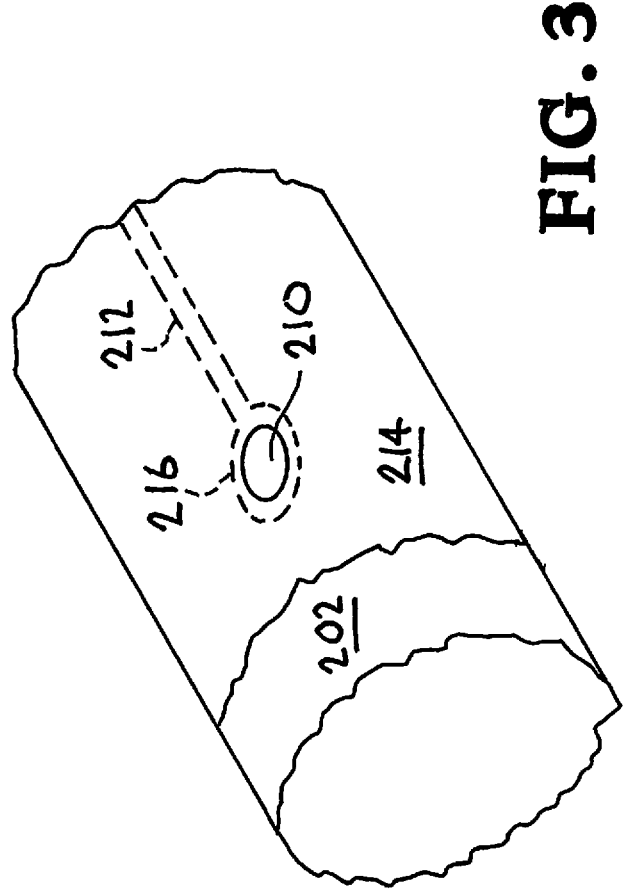
FIG. 3 shows the protective coating with openings for the sensors.

Referring now to FIG. 3, the fabrication of the openings in the protective coating 214 for the sensors 210 is illustrated. FIG. 3 is a partial section view of Applicant's implantable device 200 that shows the base 202 and protective coating 214 and conducting traces 212 with openings 216 to expose the sensors 210.

Referring now to FIG. 4, an embodiment of Applicant's implantable device is illustrated. This embodiment of Applicant's implantable device is designated generally by the reference numeral 400. The implantable device 400 has four in-line sensors 410 on a cylindrical base 402. The electrodes 410 have a feature size (e.g. diameter) of <10 micrometers. Electrically conducting leads 412 on the cylindrical base 410 are connected to the four in-line sensors 412. The electrically conducting leads 412 have a feature size (e.g. width) of <10 micrometers. Applicant's method of fabricating the implantable device 400 allows the electrically conducting leads 412 to be curved so that they can be aligned on the base 402. A protective coating 414 covers the electrically conducting leads 412. Openings enable the sensors 410 to be exposed. Applicant's implantable device 400 can be used for implantable biomedical devices, specifically for interfacing with neurons and other excitable cells.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. A method of fabricating an implantable device, comprising the steps of:
   providing a cylindrical base having an elongated cylindrical surface,
   providing a rotation system for rotating said cylindrical base,
   providing a deposition system for depositing material on said elongated cylindrical surface of said cylindrical base,
   using said rotation system and said deposition system to deposit a first electrode, a second electrode, a third electrode, and a fourth electrode on said elongated cylindrical surface of said cylindrical base so that said first electrode, said second electrode, said a third electrode, and said fourth electrode are aligned on said elongated cylindrical surface of said cylindrical base,
   using said rotation system and said deposition system
   to deposit a first electrically conducting lead on said elongated cylindrical surface of said cylindrical base in a manner that allows said first electrically conducting lead to be curved and connected to said first electrode,
   to deposit a second electrically conducting lead on said elongated cylindrical surface of said elongated cylindrical base in a manner that allows said second electrically conducting lead to be curved and connected to said second electrode,
   to deposit a third electrically conducting lead on said elongated cylindrical surface of said cylindrical base in a manner that allows said third electrically conducting lead to be curved and connected to said third electrode,
   to deposit a fourth electrically conducting lead on said elongated cylindrical surface of said cylindrical base in a manner that allows said second electrically conducting lead to be curved and connected to said fourth electrode, and
   using said rotation system and said deposition system to deposit a protective coating on said elongated cylindrical surface of said cylindrical base covering said first electrically conducting lead, said second electrically conducting lead, said third electrically conducting lead, and said fourth electrically conducting lead.

2. The method of fabricating an implantable device of claim 1 wherein said step of using said rotation system and said deposition system to deposit a first electrode, a second electrode, a third electrode, and a fourth electrode on said elongated cylindrical surface of said cylindrical base so that said first electrode, said second electrode, said a third electrode, and said fourth electrode are aligned on said elongated cylindrical surface of said cylindrical base produces four in-line sensors with one side and with another side and wherein a first section of said elongated cylindrical surface of said cylindrical base is on said one side of said four in-line sensors and a second section of said elongated cylindrical surface of said cylindrical base is on said other side of said four in-line sensors, and
   wherein said step of using said rotation system and said deposition system to deposit a first electrically conducting lead on said elongated cylindrical surface of said cylindrical base comprises using said rotation system and said deposition system to deposit a first electrically conducting lead on said first section of said elongated cylindrical surface of said cylindrical base, and
   wherein said step of using said rotation system and said deposition system to deposit a second electrically conducting lead on said elongated cylindrical surface of said cylindrical base comprises using said rotation system and said deposition system to deposit a second electrically conducting lead on said first section of said elongated cylindrical surface of said cylindrical base,
   wherein said step of using said rotation system and said deposition system to deposit a third electrically conducting lead on said elongated cylindrical surface of said cylindrical base comprises using said rotation system and said deposition system to deposit a third electrically conducting lead on said second section of said elongated cylindrical surface of said cylindrical base, and wherein said step of using said rotation system and said deposition system to deposit a fourth electrically conducting lead on said elongated cylindrical surface of said cylindrical base comprises using said rotation system and said deposition system to deposit a fourth electrically conducting lead on said second section of said elongated cylindrical surface of said cylindrical base.

3. The method of fabricating an implantable device of claim 1 wherein said step of using said rotation system and said deposition system to deposit a first electrically conducting lead on said elongated cylindrical surface of said cylindrical base in a manner that allows said first electrically conducting lead to be curved and connected to said first electrode, to deposit a second electrically conducting lead on said elongated cylindrical surface of said cylindrical base in a manner that allows said second electrically conducting lead to be curved and connected to said second electrode, to deposit a third electrically conducting lead on said elongated cylindrical surface of said cylindrical base in a manner that allows said third electrically conducting lead to be curved and connected to said third electrode, to deposit a fourth electrically conducting lead on said elongated cylindrical surface of said cylindrical base in a manner that allows said second electrically conducting lead to be curved and connected to said fourth electrode comprises using said rotation system and said deposition system to deposit a first electrically conducting lead having a feature size of <10 micrometers, to deposit a second electrically conducting lead having a feature size of <10 micrometers, to deposit a third electrically conducting lead having a feature size of <10 micrometers, and to deposit a fourth electrically conducting lead having a feature size of <10 micrometers.

4. The method of fabricating an implantable device of claim 1 wherein said step of using said rotation system and said deposition system to deposit a first electrode, a second electrode, a third electrode, and a fourth electrode on said base comprises using said rotation system and said deposition system to deposit a first electrode, a second electrode, a third electrode, and a fourth electrode each having a feature size of <10 micrometers.

5. The method of fabricating an implantable device of claim 1 wherein said step of using said rotation system and said deposition system to deposit a first electrically conducting lead on said elongated cylindrical surface of said base in a manner that allows said first electrically conducting lead to be curved and connected to said first electrode, to deposit a second electrically conducting lead on said elongated cylindrical surface of said cylindrical base in a manner that allows said second electrically conducting lead to be curved and connected to said second electrode, to deposit a third electrically conducting lead on said elongated cylindrical surface of said cylindrical base in a manner that allows said third electrically conducting lead to be curved and connected to said third electrode, to deposit a fourth electrically conducting lead on said elongated cylindrical surface of said cylindrical base in a manner that allows said second electrically conducting lead to be curved and connected to said fourth electrode comprises using said rotation system and said deposition system to deposit a first electrically conducting metal lead,
to deposit a second electrically conducting metal lead,
to deposit a third electrically conducting metal lead,
to deposit a fourth electrically conducting metal lead.

6. The method of fabricating an implantable device of claim 1 wherein said step of using said rotation system and said deposition system to deposit a first electrically conducting lead on said elongated cylindrical surface of said base in a manner that allows said first electrically conducting lead to be curved and connected to said first electrode, to deposit a second electrically conducting lead on said elongated cylindrical surface of said cylindrical base in a manner that allows said second electrically conducting lead to be curved and connected to said second electrode, to deposit a third electrically conducting lead on said elongated cylindrical surface of said cylindrical base in a manner that allows said third electrically conducting lead to be curved and connected to said third electrode, to deposit a fourth electrically conducting lead on said elongated cylindrical surface of said cylindrical base in a manner that allows said second electrically conducting lead to be curved and connected to said fourth electrode comprises using said rotation system and said deposition system to deposit a first electrically conducting polymer lead,
to deposit a second electrically conducting polymer lead,
to deposit a third electrically conducting polymer lead,
to deposit a fourth electrically conducting polymer lead.

7. The method of fabricating an implantable device of claim 1 wherein said step of using said rotation system and said deposition system to deposit a first electrode, a second electrode, a third electrode, and a fourth electrode on said base comprises using said rotation system and said deposition system to deposit a first conducting metal electrode, a second conducting metal electrode, a third conducting metal electrode, and a fourth electrically conducting metal electrode on said base.

8. The method of fabricating an implantable device of claim 1 wherein said step of using said rotation system and said deposition system to deposit a first electrode, a second electrode, a third electrode, and a fourth electrode on said base comprises using said rotation system and said deposition system to deposit a first conducting polymer electrode, a second conducting polymer electrode, a third conducting polymer electrode, and a fourth electrically conducting polymer electrode on said base.

9. A method of fabricating an implantable device, comprising the steps of:

providing a cylindrical base having a cylindrical surface,
providing a rotation system for rotating said cylindrical base,
providing a coating system for coating said cylindrical surface of said cylindrical base,
providing an ablating system for abating portions of said coating, using said rotation system, said coating system, and said ablating system to form a first electrode on said base, to form a second electrode on said base, to form a third electrode on said base, and to form a fourth electrode on said base with said first electrode, said second electrode, said third electrode, and said fourth electrode being aligned on said cylindrical base, using said rotation system, said coating system, and said ablating system to form a first electrically conducting lead on said base in a manner that allows said first electrically conducting lead to be curved and connected to said first electrode, using said rotation system, said coating system, and said ablating system to form a second electrically conducting lead on said base in a manner that allows said second electrically conducting lead to be curved and connected to said second electrode, using said rotation system, said coating system, and said ablating system to form a third electrically conducting lead on said base in a manner that allows said third electrically conducting lead to be curved and connected to said third electrode, using said rotation system, said coating system, and said ablating system to form a fourth electrically conducting lead on said base in a manner that allows said fourth electrically conducting lead to be curved and connected to said fourth electrode, and using said rotation system and said coating system deposit a protective coating on said base covering said first electrically conducting lead, said second electrically conducting lead, said third electrically conducting lead, and said fourth electrically conducting lead.

10. The method of fabricating an implantable device of claim 9 wherein said step of using said rotation system, said coating system, and said ablating system to form a first electrode on said base, to form a second electrode on said base, to form a third electrode on said base, and to form a fourth electrode on said base with said first electrode, said second electrode, said third electrode, and said fourth electrode being aligned on said cylindrical surface of said cylindrical base produces four in-line sensors with one side and with another side and wherein a first section of said cylindrical surface of said cylindrical base is on said one side of said four in-line sensors and a second section of said cylindrical surface of said cylindrical base is on said other side of said four in-line sensors, and wherein said steps of using said rotation system, said coating system, and said ablating system to form a first electrically conducting lead on said base in a manner that allows said first electrically conducting lead to be curved and connected to said first electrode on said first section, using said rotation system, said coating system, and said ablating system to form a second electrically conducting lead on said base in a manner that allows said second electrically conducting lead to be curved and connected to said second electrode on said first section, using said rotation system, said coating system, and said ablating system to form a third electrically conducting lead on said base in a manner that allows said third electrically conducting lead to be curved and connected to said third electrode on said second section, and using said rotation system, said coating system, and said ablating system to form a fourth electrically conducting lead on said base in a manner that allows said fourth electrically conducting lead to be curved and connected to said fourth electrode on said second section.

11. The method of fabricating an implantable device of claim 9 wherein said step of using said rotation system, said coating system, and said ablating system to form electrically conducting leads on said base comprises using said rotation system, said coating system, and said ablating system to form electrically conducting leads on said base having a feature size of <10 micrometers.

12. The method of fabricating an implantable device of claim 9 wherein said step of using said rotation system, said coating system, and said ablating system to form electrodes on said base comprises using said rotation system, said coating system, and said ablating system to form electrodes on said base having a feature size of <10 micrometers.

13. The method of fabricating an implantable device of claim 9 wherein said step of using said rotation system, said coating system, and said ablating system to form electrically conducting leads on said base comprises using said rotation system, said coating system, and said ablating system to form conducting metal leads on said base.

14. The method of fabricating an implantable device of claim 9 wherein said step of using said rotation system, said coating system, and said ablating system to form electrically conducting leads on said base comprises using said rotation system, said coating system, and said ablating system to form electrically conducting polymer leads on said base.

15. The method of fabricating an implantable device of claim 9 wherein said step of using said rotation system and said deposition system to deposit electrodes on said base comprises using said rotation system and said deposition system to deposit electrical conducting metal electrodes on said base.

16. The method of fabricating an implantable device of claim 9 wherein said step of using said rotation system and said deposition system to deposit electrodes on said base comprises using said rotation system and said deposition system to deposit electrical conducting polymer electrodes on said base.

* * * * *